(12) United States Patent
Bodmeier

(10) Patent No.: US 7,303,756 B1
(45) Date of Patent: *Dec. 4, 2007

(54) MULTIPHASE SYSTEM

(75) Inventor: Roland Bodmeier, Berlin (DE)

(73) Assignee: Bertex Pharma GmbH, Berlin (DE)

( * ) Notice: Subject to any disclaimer, the term of this patent is extended or adjusted under 35 U.S.C. 154(b) by 564 days.

This patent is subject to a terminal disclaimer.

(21) Appl. No.: 09/445,311

(22) PCT Filed: Jun. 5, 1998

(86) PCT No.: PCT/DE98/01589

§ 371 (c)(1),
(2), (4) Date: May 17, 2000

(87) PCT Pub. No.: WO98/55100

PCT Pub. Date: Dec. 10, 1998

(30) Foreign Application Priority Data

Jun. 5, 1997  (DE) ................................. 197 24 784
Mar. 13, 1998  (DE) ................................. 198 11 951

(51) Int. Cl.
*A61F 13/00* (2006.01)
*A61K 9/14* (2006.01)
*A61K 9/16* (2006.01)

(52) U.S. Cl. .................. 424/422; 424/489; 424/491

(58) Field of Classification Search ............. 424/422, 424/426, 430–438, 489, 491–502; 514/938
See application file for complete search history.

(56) References Cited

U.S. PATENT DOCUMENTS

| | | | | |
|---|---|---|---|---|
| 3,678,149 A * | 7/1972 | Prigal | .................. | 424/275.1 |
| 4,188,373 A | 2/1980 | Krezanoski | .................. | 514/11 |
| 4,454,110 A | 6/1984 | Caslavsky | .................. | 424/54 |
| 4,938,763 A | 7/1990 | Dunn et al. | .............. | 604/891.1 |
| 4,954,298 A * | 9/1990 | Yamamoto et al. | .......... | 264/4.6 |
| 5,077,049 A | 12/1991 | Dunn et al. | .................. | 424/426 |
| 5,081,156 A | 1/1992 | Yamahira et al. | .......... | 514/773 |
| 5,278,201 A | 1/1994 | Dunn et al. | .................. | 523/113 |
| 5,278,202 A | 1/1994 | Dunn et al. | .................. | 523/113 |
| 5,288,502 A * | 2/1994 | McGinity et al. | ........... | 424/484 |
| 5,324,519 A | 6/1994 | Dunn et al. | .................. | 424/426 |
| 5,324,520 A | 6/1994 | Dunn et al. | .................. | 424/435 |
| 5,340,849 A | 8/1994 | Dunn et al. | .................. | 523/113 |
| 5,368,859 A | 11/1994 | Dunn et al. | .................. | 424/426 |
| 5,487,897 A | 1/1996 | Polson et al. | ............... | 424/426 |
| 5,595,760 A | 1/1997 | Cherif-Cheikh | ............. | 424/464 |
| 5,599,552 A | 2/1997 | Dunn et al. | .................. | 424/423 |
| 5,632,727 A | 5/1997 | Tipton et al. | .................. | 602/47 |
| 5,639,796 A * | 6/1997 | Lee | ........................... | 514/773 |
| 5,654,008 A | 8/1997 | Herbert et al. | .............. | 424/489 |
| 5,681,873 A | 10/1997 | Norton et al. | .............. | 523/115 |
| 5,690,954 A * | 11/1997 | Illum | ........................ | 424/434 |
| 5,702,716 A | 12/1997 | Dunn et al. | .................. | 424/422 |
| 5,707,647 A | 1/1998 | Dunn et al. | .................. | 424/443 |
| 5,717,030 A | 2/1998 | Dunn et al. | .................. | 523/111 |
| 5,722,950 A | 3/1998 | Fujita et al. | .................. | 604/48 |
| 5,725,491 A | 3/1998 | Tipton et al. | .................. | 602/43 |
| 5,733,950 A | 3/1998 | Dunn et al. | .................. | 523/113 |
| 5,736,152 A | 4/1998 | Dunn et al. | .................. | 424/426 |
| 5,739,176 A | 4/1998 | Dunn et al. | .................. | 523/113 |
| 5,744,153 A | 4/1998 | Yewey et al. | ............... | 424/426 |
| 5,747,058 A | 5/1998 | Tipton et al. | ............... | 424/423 |
| 5,759,563 A | 6/1998 | Yewey et al. | ............... | 424/426 |
| 5,780,044 A | 7/1998 | Yewey et al. | ............... | 424/426 |
| 5,783,205 A | 7/1998 | Berggren et al. | ........... | 424/426 |
| 5,792,469 A | 8/1998 | Tipton et al. | ............... | 424/422 |
| 5,945,115 A * | 8/1999 | Dunn et al. | .................. | 424/422 |
| 5,980,945 A | 11/1999 | Ruiz | .......................... | 424/484 |
| 6,554,503 B2 * | 4/2003 | Imanari et al. | ............. | 396/531 |
| 2003/0152634 A1* | 8/2003 | Bodmeier | ................... | 424/489 |
| 2004/0010224 A1* | 1/2004 | Bodmeier | ................... | 604/82 |

FOREIGN PATENT DOCUMENTS

EP  92116802.7  5/1993
JP  07025905 A *  7/1995

* cited by examiner

*Primary Examiner*—Lakshmi S. Channavajjala
(74) *Attorney, Agent, or Firm*—Rick Matos; Innovar, LLC

(57) ABSTRACT

The invention relates to a preparation comprising a carrier phase and at least one further phase which cannot be mixed with the carrier phase or only partially mixed therewith, wherein the change in ambient conditions alters the viscosity of the carrier phase. The invention also relates to a method for the production thereof and to particles and implants containing said preparations. The inventive preparations can contain various active substances with a delayed release action.

65 Claims, No Drawings

MULTIPHASE SYSTEM

BACKGROUND OF THE INVENTION

The invention provides a composition comprising a carrier phase and at least one additional phase, said at least one additional phase being immiscible with the carrier phase or being partially miscible with the carrier phase, whereby a change in ambient conditions alters the viscosity of the carrier phase.

Drugs can be administered parenterally as a depot formulation for the treatment of certain diseases. Besides classical dosage forms, such as oily suspensions, modern dosage forms on the basis of biocompatible/biodegradable polymers can be used. The implants (single-unit systems) or microparticles (multiparticulate systems) are prepared from the solid polymeric carriers and are then placed in the body by implantation or injection.

For the implant preparation, the drug is mixed with the carrier (e.g., a polymer) and is then processed into the desired implant shape (e.g., cylinder, pellet, film, fiber), for example, by extrusion or compression at elevated temperatures. Such solid implants are then usually placed in the body by a surgical procedure or through hollow needles with a large diameter.

Drug-containing microparticles can be used in order to circumvent such surgical procedures with implants, which are highly undesired by patients. Suspensions of these particles can be injected with a syringe through an injection needle. These microparticles are prepared outside the body by various processes, such as, for example, the solvent evaporation technique, the organic phase separation technique, or a spray-drying technique. In the solvent evaporation method, which is frequently used for the preparation of biodegradable microparticles, a drug is dissolved or dispersed in a solution of a biodegradable polymer (e.g., polylactic acid) in a solvent (e.g. methylene chloride), which is not miscible with water. This drug-containing polymer phase is then emulsified in an external aqueous phase and forms drug-containing polymer droplets. The microparticles are obtained after evaporation of the solvent through the solidification of the polymer and are then separated from the aqueous phase (e.g., by filtration) and dried.

Commercially available biodegradable microparticle products (e.g., Decapeptyl, Enantone) consist of a dry powder of the microparticles and an aqueous suspension vehicle. The microparticles and the aqueous suspension vehicle are stored separately, for example, in two-chamber syringes or in two ampoules, because of the hydrolytic instability of the biodegradable polymers. The microparticles are then suspended in the aqueous suspension vehicle just prior to the administration and are then injected.

The preparation of these biodegradable particle products is very elaborate and has to be done under sterile or aseptic conditions. In addition, most microencapsulation processes are difficult or not at all transferable to the production size and are dependent on many process and formulation variables. The suspension of the microparticles and the subsequent injection can also cause difficulties (e.g., agglomeration, residual microparticles in the syringe, clogging of the needle, etc.).

Besides the water-insoluble polyactic acid derivatives and other water-insoluble polymers, hydrophilic polymers can also be used as carrier materials for microparticles and implants. Microparticles of hydrophilic polymers (e.g., polysaccharides, such as alginates or chitosan, cellulose derivatives, protein-(collagen) derivatives) can be prepared, for example, through spray-drying or w/o-emulsification techniques, whereby the drug-containing aqueous polymer solution is either spray-dried or emulsified into an external oil phase, whereby the particles are obtained after removal of the water, washing, filtration and drying. Like the processes for the preparation of polyactic acid microparticles, the microencapsulation techniques with the hydrophilic polymers are also very elaborate.

A composition based on a drug-containing polymer solution was developed in order to avoid problems with the preparation and administration of implants or microparticles U.S. Pat. No. 4,938,763). Thereby, a solution of polylactic acid (or a derivative) is injected into the body, for example, intramuscularly or subcutaneously, and an implant is formed in-situ through the precipitation of the polymer in the tissue. The implant is therefore not formed outside, but inside the body. The polymer solution has to be injectable through a needle; it therefore cannot be too viscous. The possible polymer content is therefore primarily limited through the viscosity of the polymer solution and not through the solubility of the polymer. In addition, precipitation of the polymer during the injection of the polymer solution can negatively influence the injection of the remaining polymer solution. Disadvantages of this method are also the use of high amounts of solvents with toxicity and compatibility problems and, after injection into soft tissue, the somewhat uncontrollable solidification of the polymer with a not exactly defined surface area of the implant. This can lead to irreproducible release profiles. In addition, the drug can be released rapidly prior to the solidification of the polymer solution. This so-called burst-effect is usually undesirable.

Some systems were developed, whereby a solidification/viscosity increase of drug-containing polymer solutions after administration/injection in the body was caused primarily by a temperature-change or by a pH-change or by special substances (e.g., ions), and not by diffusion of the solvent. These systems have the same disadvantages as the system described in the previous paragraph.

SUMMARY OF THE INVENTION

It is an object of the invention to provide a composition, which is simple to prepare and which avoids the problems seen in the development and the administration of microparticles and implants, including the described in-situ implants.

This object is achieved by providing a composition comprising a carrier phase and at least one additional phase, said at least one additional phase being immiscible with the carrier phase or being only partially miscible with the carrier phase, whereby a change in ambient conditions alters (preferably increases) the viscosity of the carrier phase.

According to the invention, the composition comprises a dispersion of an inner carrier phase and a second external phase, said second external phase being immiscible with the inner carrier phase or being partially miscible with the inner carrier phase. Particles or an implant are formed after a change in the ambient conditions, the change in ambient conditions resulting in an increase in the concentration of the carrier material in the carrier phase, in a precipitation of the carrier material, or in a diffusion of the solvent out of the carrier phase.

The change in ambient conditions is caused by the contact of the composition with body components or with substances present at the administration site or by a change in temperature, such as an increase in temperature, by a pH-change, by a change in ionic strength or type of ion, or by a combination of two or more changes in ambient conditions.

The composition is prepared through high pressure homogenization. The particle size of the carrier phase is primarily smaller than 100 µm, preferably smaller than 20 µm, and is primarily in the colloidal size range. The composition is prepared just prior to administration, and the carrier phase and the second phase are either stored separately from each other or in contact with each other but in a non-dispersed or only partially dispersed state. The carrier material is a water-insoluble polymer, a polymer which is soluble in aqueous fluids, a water-soluble polymer, a cellulose-derivative or acrylate-derivative, a biocompatible and/or biodegradable polymer, polylactide or a polylactide-derivative, a polysaccharide, a protein, a lipid, or a combination of carrier materials. Where the carrier material is dissolved and/or dispersed in the carrier phase, the carrier phase comprises a carrier melt.

According to the invention, the composition further comprises at least one active compound, the active compound being a drug, such as a peptide-drug or protein drug. In such a case, the active compound is dissolved, dispersed, suspended or emulsified in the carrier phase. The active compound may additionally or exclusively be present in the other phases.

According to the invention, the carrier phase comprises water or an organic solvent, such as ethanol, acetone, butanol, ethylformate, pentanol, n- or i-propanol, tetrahydrofuran, triethylcitrate, triacetin, propylene glycol, glycerol, polyethylene glycol, ethylacetate, methylacetate, dimethylformamide, dimethylsulfoxide, dimethylacetamide, 2-pyrrolidone, N-methyl-2-pyrrolidone or a mixture of two or more of the above mentioned solvents. The second phase is fully, partially or not miscible with aqueous fluids. The composition comprises a third phase, the carrier phase and the second phase being mixed with the additional third phase. The second phase is not or is only partially miscible with the third phase, the third phase being fully, partially or not miscible with aqueous fluids. The second phase comprises semisynthetic or synthetic lipids, oil or waxes, such as cottonseed oil, soybean oil, safflower oil, hydrated peanut oil, olive oil, castor oil, tryglyceride mixtures (like Miglyol), silicone oil, isopropylmyristate, ethyloleate, paraffin, glycerol, propylene glycol, polyethylene glycol or mixtures of two or more of the above mentioned substances.

According to the invention, the composition may have thixotropic rheological behavior and may additionally include viscosity-increasing substances. It may further comprise stabilizers, release modifying agents, which affect the residence time at the site of administration, bioadhesive materials, or penetration enhancers.

A composition according to the invention results in the active compound being released in an extended release fashion at the site of administration so that an initial rapid release of the active compound at the site of administration is avoided.

The site of administration of the composition according to the invention is live or dead biological tissue.

The administration of the composition according to the invention is suitable for the parenteral, peroral, subcutaneous, rectal, buccal, vaginal, nasal, local, sublingual, periodontal, or transdermal administration. According to the invention, the composition is thereby placed into body cavities.

The composition according to the invention may be in the form of a capsule.

A composition according to the invention is, for example, a dispersion comprising an inner, active compound-containing carrier phase and an external second phase.

This invention also includes a method of preparing a composition according to the invention, whereby a mixture of a liquid carrier phase and a second phase is prepared and whereby this mixture is placed into a living body and forms particles.

DETAILED DESCRIPTION OF PREFERRED EMBODIMENTS

According to the invention, the carrier phase is immiscible with the second phase or is only partially miscible with the second phase, the carrier phase forming particles and being the inner phase of a dispersion. The composition is prepared with high pressure homogenization or under heating.

The particle size of the carrier phase is smaller than 200 µm and is in the colloidal size range. The composition is prepared from the carrier phase and the external phase just prior to placement into the body, the carrier phase and the external phase being stored separately from each other, being stored in a two chamber syringe, or being stored in contact, but not or only partially in a dispersed state. Where the carrier material is dissolved in the carrier phase, the carrier material is a water insoluble polymer, a cellulose derivative, an acrylate derivative, a biocompatible or a biodegradable polymer, polylactide or a polylactide-glycolide copolymer. The solvent for the carrier material is an organic solvent or is a solvent mixture, the solvent being miscible with water, the second phase not being miscible with water or being only partially miscible with water.

According to the invention, the second phase, which is miscible with water, comprises natural, semisynthetic or synthetic lipids, oils, or waxes. The composition, which may have thixotropic rheological behavior, may further include viscosity increasing substances, stabilizers or release modifying agents.

According to the invention, a process is preferred, whereby the active compounds are added to the composition, whereby the active compounds are dissolved, dispersed, suspended, or emulsified in the carrier phase, whereby the active compounds are present in the external phase, and whereby the active compound is a peptide- or protein drug.

This invention also includes particles which are obtained through the placement of a composition according to this invention at the site of administration. The particles are therefore not prepared separately by elaborate microencapsulation techniques and are not suspended just prior to administration in the body, but the particles are formed in-situ out of the inner carrier phase after placement of the composition in the body. The term "particle" is used for pellets, micro- and nanoparticles. Particles can also consist of agglomerates of smaller particles.

This invention also includes an implant, which is obtained through the placement of a composition according to this invention at the site of administration. This implant is preferably formed in a living tissue through injection, whereby the implant is formed through a viscosity change of the composition. This implant comprises preferably drugs, which are then released over a longer period of time into the tissue. An implant may also be formed through the partial coalescence of the carrier phase.

According to the invention, a change in the ambient conditions is an increase in concentration of the carrier material in the carrier phase, a precipitation of the carrier material, a diffusion of the solvent out of the carrier phase, a contact of the carrier phase with ambient components, a temperature change, a change in pH-value, a change in ionic strength, the placement of the composition at the site of administration or a combination of 2 or more of the mentioned ambient conditions.

For example, in the case of a temperature increase, the inner carrier phase may transform from a sol in a gel state and therefore be solidified after placement in the body through warming to body temperature. Excipients may be incorporated which accelerate or retard the solidification. The composition may also be heated just prior to the administration. In addition, the viscosity change of the carrier phase may be caused through a pH-change or through substances present at the site of administration, such as ions.

For example, an active compound-containing dispersion comprising an inner carrier phase and a second external phase (e.g., an oil) may be prepared and be placed into the body. The inner phase then solidifies, for example, through solvent diffusion in the environment or diffusion of body fluids into the carrier phase or through a change in temperature, pH-value or ionic strength. For example, in the case of biodegradable polymers, the dispersion may be injected i.m. or s.c.; in the case of peroral administration, the liquid dispersion can be filled into capsules. The inner phase may solidify in contact with body fluids and can form, for example, particles.

The carrier phase is preferably placed into the body in a liquid/semisolid, and not in a solid form like in the case of microparticles or implants. The carrier material-containing phase of the composition then solidifies in the body, and the active component is then slowly released. This method is basically a preparation of a dispersion/emulsion. The elaborate preparation of microparticles or implants or the resuspension of particles prior to the administration is not necessary.

The compositions may be prepared from the carrier phase, the second phase and, possibly, the third phase through processes which are known to those skilled in the art. The preparation of liquid or semisolid compositions falls in the area of classical pharmaceutical processing techniques. The particle size and particle size distribution of the inner phase and, therefore, also indirectly of the solidified particles may be influenced in particular through the type and intensity of the emulsification process. Besides the emulsification process, other parameters also influence the particle size, such as the choice of an emulsifying agent or a complex of emulsifying agents, and the viscosity of the inner phase and the outer phase. Dispersions with a smaller particle size (e.g. in the colloidal particle size range) may, for example, be obtained by high pressure homogenization. The compositions may also be prepared under heat or through phase inversion.

The compositions may also be prepared just prior to the administration. The individual phases or single components (e.g. the active compound) may be stored separately or partially separated from each other, e.g. in a two chamber syringe or in special containers which allow an efficient mixing of the phases. This is especially advantageous for systems with physical or chemical stability problems.

The carrier material of the carrier phase is preferably a water-insoluble polymer, a polymer which is soluble in aqueous fluids, or a water-soluble polymer of synthetic, semisynthetic or natural origin. This includes cellulose derivatives (e.g., celluloseacetate, ethylcellulose, cellulose-acetephthalate), acrylate-derivatives (e.g., Eudragite, poly (methylmethacrylate), cyanoacrylate) and also biocompatible and biodegradable polymers like polyanhydrides, polyesters, polyorthoesters, polyurethanes, polycarbonates, polyphosphazenes, and polyacetals. Important are polyesters, such as polylactide, polylactide-glycolides, polycaprolactone, polyhydroxybutyrate- or valerate. In addition, polysaccharides, such as sodium alginate, chitosan, or chitin, or proteins may be used. Obviously, combinations of the carrier materials including co-polymers or terpolymers may be used. Lipids are also suitable carrier materials.

According to the invention, the carrier material is dissolved, molten or dispersed in the carrier phase. The carrier material is mostly responsible for the viscosity change as a result of a change in ambient conditions.

According to the invention, the carrier material by itself may form the carrier phase. The carrier material then has a semi-solid consistency by itself. The addition of solvents is not necessary.

The maximum concentration of carrier material which may be used depends primarily on the viscosity of the carrier phase and the intensity of the dispersion equipment. Although the carrier phase by itself is not sufficiently flowable and therefore injectable, for example, for parenteral injection, it may be incorporated into the external flowable phase. An injectable composition may then be obtained. In comparison to injectable polymer solutions, significantly higher concentrated polymer solutions and, therefore, less solvent may be used with this technology.

It is especially desired that the composition according to the invention comprises additionally at least one active compound. The active compounds comprise low or higher molecular weight drugs (e.g. also peptides, proteins, oligonucleotides) for human- and veterinary administration and substances which are used for agricultural purposes, in households, in the food, cosmetic or chemical industries and other industrial branches. Preferably, the active compound is dissolved in the carrier phase. It is also preferred that the active compound be dispersed, suspended or emulsified in the carrier phase. It is also preferred that the active component be present additionally or exclusively in the other phases. For example, a part of the active component may be added to the external phase to achieve an initial dose. Obviously, also combinations of active compounds may be used.

It is also preferred that the carrier phase comprise water or an organic solvent, such as ethanol, acetone, butanol, ethylformate, pentanol, n-propanol, i-propanol, tetrahydrofuran, triethylcitrate, triacetin, propylene glycol, glycerol, polyethylene glycol, ethylacetate, methylacetate, dimethylformamide, dimethylsulfoxide, dimethylacetamide, 2-pyrrolidone, N-methyl-2-pyrrolidone or a mixture of two or more of these solvents. In particular, solvents listed in the "draft guideline of the international conference on harmonization on impurities—residual solvents" may be used. Solvent mixtures may also be used, selected for example with regard to their solvent quality for the polymer or miscibility with aqueous and oily phases. The choice of solvent may, for example, influence the miscibility of the carrier liquid with body fluids, the external phase and the solidification of the carrier phase. The viscosity of the carrier phase may be influenced by the carrier material (e.g. molecular weight, concentration etc.) and also by the solvent. The degree of solidification may be influenced by the selection of the polymer, the solvent and the external phase.

It is preferred that the second phase be completely, partially or not miscible with aqueous fluids.

According to the invention, the second phase comprises natural, semisynthetic or synthetic lipids, oils or waxes, such as cottonseed oil, soybean oil, safflower oil, hydrated peanut oil, olive oil, castor oil, triglyceride mixtures (like Miglyol), silicone oil, isopropylmyristate, ethyloleate, paraffin, glycerol, propylene glycol, polyethylene glycol or mixtures of two or more of the above-listed substances.

According to the invention, the composition comprises a third phase. It is thereby preferred that the carrier phase and the second phase be mixed with the additional third phase. It is also preferred that the second phase not be miscible or be only partially miscible with the third phase. It is also preferred that the third phase be completely, partially or not miscible with aqueous fluids. Various variations of multidispersed systems are therefore possible.

According to the invention, compositions are preferred whereby at least one of the phases contains viscosity increasing substances, stabilizers, release modifying agents, substances which increase or decrease the residence time at the site of administration, bioadhesive materials, penetration enhancers, substances which retard the drug release, substances which increase or which avoid the initial rapid release of the active compound or any combination of the above-mentioned substances.

Viscosity increasing substances, e.g. fatty acids salts with multivalent cations, polymers, silicon derivatives or higher melting lipids, may be added to the composition. The rheological behavior of the external phase may also be changed through additives, for example, a phase may be formed, whereby the viscosity is decreased during the injection and increased during the storage phase (thixotropic rheological behavior).

Stabilizers, such as emulsifying agents, may be necessary for the preparation of the dispersion. The emulsifying agents include among other polyethyleneglycol-fatty acid esters, -fatty acid ethers, -sorbitan fatty acid esters, sorbitan fatty acid esters, partial fatty acid esters of multivalent alcohols or sugars, lecithins and poloxamers.

The residence time of the composition at the site of administration may be prolonged through suitable substances, e.g. bioadhesive materials. These substances may be added either to the carrier phase and/or to the other phases. In addition, penetration enhancers may be added, which improve the absorption of the active compound.

The release of the active compound may be influenced, for example, through the degree of dispersity, the loading of the active component, the polymer, the polymer concentration, and the molecular weight of the polymer. In addition, release modifying agents, such as hydrophilic or lipophilic substances of inorganic, organic or polymeric nature, can also be incorporated. A special advantage of the compositions according to this invention is that, in comparison to active compound-containing polymer solutions, which form an implant in-situ, an initial rapid release of the active component may be avoided at the site of administration. The active component-containing carrier phase represents the internal phase of the composition and is therefore not primarily in contact with the surrounding body immediately after administration.

According to the invention, the site of administration is living or dead biological tissue.

The composition according to this invention is preferably directed to the parenteral, peroral, subcutaneous, rectal, buccal, vaginal, local, sublingual, peridontal or transdermal route of administration.

Multi-particulate systems in the form of pellets or micro-/nanoparticles gain more and more importance also with peroral administration in comparison to the so-called "single-unit" systems such as tablets or capsules. Besides the parenteral administration, the compositions may therefore also be used especially for peroral applications, but also for the application in different body cavities (e.g. rectal, vaginal or peridontal). The compositions of this invention can be filled into a syringe or an ampoule or into a capsule for the preparation of the final dosage form.

Besides the application of the compositions in the pharmaceutical area, they may also be used in other areas where the active compound may be released in a predetermined manner to the surrounding environment over a longer time period. These systems may be, for example, long-term fertilizer, insecticides or pheromones for the treatment of plants. The terms "ambient conditions" and "site of administration" as used in this invention are broad and are not restricted to the use in the medical area.

The following examples illustrate the invention; however, it should be understood that they should not limit its use.

EXAMPLE 1

Poly(d,1-lactid)(Resomer-203, Boehringer Ingelheim) is dissolved in dimethylsulfoxide (DMSO) and PEG400 and Tween 80. Aluminum stearate (2%) is incorporated into peanut oil under warming, the temperature is then lowered and Span 80 is added. This polymer phase is emulsified into the second phase for the formation of an emulsion. Alternatively to DMSO, N-Methyl-2-pyrrolidone may be used as solvent.

EXAMPLE 2

Poly (d,1-lactid)(Resomer-203, Boehringer Ingelheim) is dissolved in triethylcitrate and Tween 80 (3% based on the inner phase). This polymer phase is emulsified in glycerol for the formation of a dispersion.

EXAMPLE 3

Poly(oxyethylene-oxypropylene)(Lutrol F 127 (BASF)) is dissolved in water (>20% w/w) and is emulsified into the external peanut oil phase. Increasing the temperature to 37° C. leads to an increase in viscosity of the inner phase.

EXAMPLE 4

Chitosan is dissolved in an acidic aqueous medium or a chitosan salt (e.g. chitosan glutamate) is dissolved in water. This solution is emulsified into the external oil phase. Chitosan precipitates in contact with pH 7.4 buffer.

The invention claimed is:

1. A method of forming a solid implant or solid microparticles in a subject, the method comprising the steps of:
  a) providing a liquid polymer-containing carrier phase, a second phase and optionally at least one active compound, said second phase being capable of forming a dispersion with the carrier phase;
  b) mixing the liquid polymer-containing carrier phase and the second phase to form a dispersion, said liquid polymer-containing carrier phase being the internal phase and said second phase being the external phase of the dispersion; and
  c) administering the dispersion to a subject thereby solidifying the polymer-containing carrier phase to form the solid microparticles or a solid implant in the subject.

2. The method of claim 1 further comprising the step of changing the viscosity of the carrier phase, wherein the change in viscosity is accomplished by contacting the dispersion with the subject, changing the pH of a medium to which the dispersion is exposed, changing the temperature of a medium to which the dispersion is exposed, changing the ionic strength of a medium to which the dispersion is exposed, or a combination thereof.

3. The method of claim 1, wherein the internal carrier phase of the dispersion has a particle size primarily smaller than about 200 μm prior to administration to the subject.

4. The method of claim 1, wherein the internal carrier phase of the dispersion has a particle size primarily in the colloidal size range prior to administration to the subject.

5. The method of claim 1 prior to the step of mixing, further comprising the step of:
storing the carrier phase and second phase separately.

6. The method of claim 1 prior to the step of mixing, further comprising the step of:
storing the carrier phase and second phase in contact with one another but in a non-dispersed or only partially dispersed state.

7. The method of claim 1 wherein the carrier phase comprises a carrier material comprising a water-soluble polymer or a polymer which is soluble in aqueous fluids.

8. The method of claim 1 wherein the carrier phase comprises a carrier material comprising a water-insoluble polymer or a lipid.

9. The method of claim 7 or 8 wherein the carrier material comprises a cellulose-derivative, acrylate-derivative, polylactide, polylactide-derivative, polysaccharide, polysaccharide-derivative, carrier melt, or a combination thereof.

10. The method of claim 1 further comprising the steps of:
providing at least one active compound; and
including the at least one active compound in the dispersion.

11. The method of claim 10 further comprising the step of:
providing a viscosity-increasing substance, stabilizer, release modifying agent, substance that affects the residence time of the microparticles or implant at the site of administration, bioadhesive material, penetration enhancers, or a combination thereof.

12. The method of claim 10 wherein the at least one active compound is released over an extended period of time at the site of administration.

13. The method of claim 10 wherein an initial rapid release of the active compound at the site of administration is avoided.

14. The method of claim 1 wherein the carrier phase comprises water, an organic solvent or a mixture thereof.

15. The method of claim 14 wherein the organic solvent is selected from the group consisting of ethanol, acetone, butanol, ethylformate, pentanol, n-propanol, iso-propanol, tetrahyrdofuran, triethylcitrate, triacetin, propylene glycol, glycerol, polyethylene glycol, ethylacetate, methylacetate, dimethylformamide, dimethylsulfoxide, dimethylacetamide, 2-pyrrolidone, N-methyl-2-pyrrolidone and a mixture thereof.

16. The method of claim 14 wherein the second phase is miscible or partially miscible with water.

17. The method of claim 14 wherein the second phase is immiscible with water.

18. The method of claim 1 wherein the second phase comprises a natural, semisynthetic or synthetic lipid, oil, wax, triglyceride, glycerol, glycol, or a mixture thereof.

19. The method of claim 18 wherein the second phase comprises cottonseed oil, soybean oil, safflower oil, hydrated peanut oil, olive oil, castor oil, Miglycol, silicone oil, isopropylmyristate, ethyloleate, paraffin, propylene glycol, poly(ethylene glycol), or a mixture thereof.

20. The method of claim 1 further comprising the steps of:
providing a third phase; and
mixing the carrier phase and the second phase or mixing the dispersion with the third phase, wherein the second phase is immiscible or only partially miscible with the third phase.

21. The method of claim 1 further comprising the step of:
providing a viscosity-increasing substance, stabilizer, release modifying agent, substance that affects the residence time of the microparticles or implant at the site of administration, bioadhesive material, penetration enhancer, or a combination thereof.

22. The method of claim 1 wherein the dispersion exhibits thixotropic rheological behavior.

23. The method of claim 1 wherein the step of administering comprises parenteral, peroral, subcutaneous, rectal, buccal, vaginal, nasal, sublingual, periodontal, or transdermal administration to the subject.

24. The method of claim 10 wherein the carrier phase comprises water, an organic solvent or a mixture thereof.

25. A system for forming solid microparticles or a solid implant in a subject, the system comprising:
an administrable dispersion;
at least one storage compartment; and
administration means; wherein
the administrable dispersion comprises a liquid polymer-containing carrier phase dispersed within a second phase and optionally comprises at least one active compound, the carrier phase being capable of forming a dispersion with the second phase;
the at least one storage compartment retains the dispersion prior to administration;
the dispersion is administrable to a subject by way of the administration means;
the dispersion has been formed by mixing the carrier phase with the second phase and thereby forming the administrable dispersion; and
the polymer-containing carrier phase in the dispersion solidifies and forms the solid microparticles or a solid implant after administration to a subject.

26. The system of claim 25 wherein the internal carrier phase of the dispersion has a particle size primarily smaller than about 200 μm prior to administration to the subject.

27. The system of claim 25 wherein the internal carrier phase of the dispersion has a particle size primarily in the colloidal size range prior to administration to the subject.

28. The system of claim 25 comprising:
a first storage compartment capable of storing the carrier phase; and
a second storage compartment capable of storing the second phase such that the carrier phase and second phase are separate; and
dispersion means adapted to form a dispersion of the carrier phase within the second phase.

29. The system of claim 25 comprising one storage component capable of storing the carrier phase and second phase, prior to dispersing, in contact with one another but in a non-dispersed or only partially dispersed state; and
dispersion means adapted to form a dispersion of the carrier phase within the second phase.

30. The system of claim 25 wherein the carrier phase comprises a carrier material comprising a water-soluble polymer or a polymer which is soluble in aqueous fluids.

31. The system of claim 25 wherein the carrier phase comprises a carrier material comprising a water-insoluble polymer or a lipid.

32. The system of claim 30 or 31 wherein the carrier material comprises a cellulose-derivative, acrylate-derivative polylactide, polylactide-derivative, polysaccharide, polysaccharide-derivative, carrier melt, or a combination thereof.

33. The system of claim 25 wherein the carrier phase comprises water, an organic solvent or a mixture thereof.

34. The system of claim 33 wherein the organic solvent is selected from the group consisting of ethanol, acetone, butanol, ethylformate, pentanol, n-propanol, iso-propanol, tetrahydrofuran, triethylcitrate, triacetin, propylene glycol, glycerol, polyethylene glycol, ethylacetate, methylacetate, dimethylformamide, dimethylsulfoxide, dimethylacetamide, 2-pyrrolidone, N-methyl-2-pyrrolidone and a mixture thereof.

35. The system of claim 25 wherein the second phase is miscible or partially miscible with water.

36. The system of claim 25 wherein the second phase is immiscible with water.

37. The system of claim 25 further comprising a third phase, wherein the third phase, the carrier phase and the second phase together form the dispersion, and the second phase is immiscible or only partially miscible with the third phase.

38. The system of claim 25 wherein the second phase comprises a natural, semisynthetic or synthetic lipid, oil, wax, triglyceride, glycerol, glycol, or a mixture thereof.

39. The system of claim 25 wherein the second phase comprises cottonseed oil, soybean oil, hydrated peanut oil, olive oil, castor oil, Miglyol, silicone oil, isopropylmyristate, ethyloleate, paraffin, propylene glycol, poly(ethylene glycol), or a mixture thereof.

40. The system of claim 25 further comprising at least one active compound in the dispersion.

41. The system of claim 40 further comprising a viscosity-increasing substance, stabilizer, release modifying agent, substance that affects the residence time of the microparticle or implant at the site of administration, bioadhesive material, penetration enhance, or a combination thereof in the dispersion.

42. The system of claim 40 wherein the at least one active compound is released over an extended period of time at the site of administration.

43. The system of claim 40 wherein an initial rapid release of at least one active compound at the site of administration is avoided.

44. The system of claim 25 further comprising a viscosity-increasing substance, stabilizer, release modifying agent, substance that affects the residence time of the microparticle or implant at the site of administration, bioadhesive material, penetration enhancers, or a combination thereof in the dispersion.

45. The system of claim 25 wherein the administration means is adapted for parenteral, peroral, subcutaneous, rectal, buccal, vaginal, nasal, sublingual, periodontal, or transdermal administration of the dispersion to a subject.

46. An administrable dispersion that forms a solid implant or solid microparticles in a subject to which it is administered, the dispersion comprising:
an internal liquid polymer-containing carrier phase dispersed within an external second phase, the carrier phase being capable of forming a dispersion with the second phase; and
optionally at least one active compound;
wherein the polymer-containing carrier phase in the dispersion solidifies and forms the solid microparticles or a solid implant after administration to a subject.

47. The dispersion of claim 46 wherein the particle size of the dispersion is primarily smaller than about 200 µm in size prior to administration to the subject.

48. The dispersion of claim 46 wherein the particle size of the dispersion is primarily in the colloidal size range prior to administration to the subject.

49. The dispersion of claim 46 wherein the carrier phase comprises a carrier material comprising a water-soluble polymer or a polymer which is soluble in aqueous fluids.

50. The dispersion of claim 46 wherein the carrier phase comprises a carrier material comprising a water-insoluble polymer.

51. The dispersion of claim 49 or 50 wherein the carrier material comprises a cellulose-derivative, acrylate-derivative, polylactide, polylactide-derivative, polysaccharide, polysaccharide-derivative, carrier melt, or a combination thereof.

52. The dispersion of claim 46 wherein the carrier phase comprises water, an organic solvent or a mixture thereof.

53. The dispersion of claim 52 wherein the organic solvent is selected from the group consisting of ethanol, acetone, butanol, ethylformate, pentanol, n-propanol, iso-propanol, tetrahydrofuran, triethylcitrate, triacetin, propylene glycol, glycerol, polyethylene glycol, ethylacetate, methylacetate, dimethylformamide, dimethylsulfoxide, dimethylacetamide, 2-pyrrolidone, N-methyl-2-pyrrolidone and a mixture thereof.

54. The dispersion of claim 46 wherein the second phase is miscible or partially miscible with water.

55. The dispersion of claim 46 wherein the second phase is immiscible with water.

56. The dispersion of claim 46 further comprising a third phase, wherein the third phase, the carrier phase and the second phase together form the dispersion, and the second phase is immiscible or only partially immiscible with the third phase.

57. The dispersion of claim 46 wherein the second phase comprised a natural, semisynthetic or synthetic lipid, oil, wax, triglyceride, glycerol, glycol, or a mixture thereof.

58. The dispersion of claim 46 wherein the second phase comprises cottonseed oil, soybean oil, safflower oil, hydrated peanut oil, olive oil, castor oil, Miglyol, silicone oil, isopropylmyristate, ethyloleate, paraffin, glycerol, propylene glycol, poly(ethylene glycol) or a mixture thereof.

59. The dispersion of claim 46 further comprising at least one active compound in the dispersion.

60. The dispersion of claim 59 further comprising a viscosity-increasing substance, stabilizer, release modifying agent, substance that affects the residence time of the microparticle or implant at the site of administration, bioadhesive material, penetration enhancer, or a combination thereof in the dispersion.

61. The dispersion of claim 59 wherein the at least one active compound is released over an extended period of time at the site of administration.

62. The dispersion of claim 59 wherein an initial rapid release of at least one active compound at the site of administration is avoided.

63. The dispersion of claim 46 further comprising a viscosity-increasing substance, stabilizer, release modifying agent, substance that affects the residence time of the microparticle or implant at the site of administration, bioadhesive material, penetration enhancer, or a combination thereof in the dispersion.

64. The dispersion of claim 46 wherein the dispersion is administered to a subject by a parenteral, peroral, subcutaneous, rectal, buccal, vaginal, nasal, sublingual, periodontal, or transdermal route.

65. The method of claim 24 wherein the organic solvent is selected from the group consisting of ethanol, acetone, butanol, ethylformate, pentanol, n-propanol, iso-propanol, tetrahydrofuran, triethylcitrate, triacetin, propylene glycol, glycerol, polyethylene glycol, ethylacetate, methylacetate, dimethylformamide, dimethylsulfoxide, dimethylacetamide, 2-pyrrolidone, N-methyl-2-pyrrolidone and a mixture thereof.

* * * * *